(12) United States Patent
Kilcher et al.

(10) Patent No.: US 8,992,224 B2
(45) Date of Patent: Mar. 31, 2015

(54) SCANNING POLYMERIZATION OF DENTAL MATERIAL

(71) Applicant: KerrHawe SA, Bioggio (CH)

(72) Inventors: Beat Kilcher, Bosco Luganese (CH); Vahik Krikorian, La Canada, CA (US)

(73) Assignee: KerrHawe SA, Bioggio (CH)

( * ) Notice: Subject to any disclaimer, the term of this patent is extended or adjusted under 35 U.S.C. 154(b) by 32 days.

(21) Appl. No.: 13/839,995

(22) Filed: Mar. 15, 2013

(65) Prior Publication Data

US 2014/0051040 A1 Feb. 20, 2014

Related U.S. Application Data

(60) Provisional application No. 61/683,556, filed on Aug. 15, 2012.

(51) Int. Cl.
*A61C 5/04* (2006.01)
*A61C 13/15* (2006.01)
*A61C 9/00* (2006.01)

(52) U.S. Cl.
CPC ............ *A61C 19/003* (2013.01); *A61C 9/0053* (2013.01); *A61C 19/004* (2013.01); *A61C 5/04* (2013.01)
USPC .......................................... 433/226; 433/215

(58) Field of Classification Search
CPC .................. A61C 19/003–19/004; A61C 5/04
USPC ........ 433/27, 29, 31, 215, 226, 227; 382/128; 607/88, 89
See application file for complete search history.

(56) References Cited

U.S. PATENT DOCUMENTS

| 4,575,805 A | * | 3/1986 | Moermann et al. ........... 700/163 |
| 4,733,660 A | | 3/1988 | Itzkan |
| 5,007,837 A | * | 4/1991 | Werly ........................... 433/226 |
| 5,738,678 A | * | 4/1998 | Patel ............................... 606/10 |
| 6,325,791 B1 | * | 12/2001 | Shimoji ............................. 606/2 |
| 6,382,967 B1 | | 5/2002 | Rohner et al. |
| 6,386,878 B1 | * | 5/2002 | Pavlovskaia et al. ......... 433/215 |
| 6,419,483 B1 | | 7/2002 | Adam et al. |
| 6,439,888 B1 | * | 8/2002 | Boutoussov et al. ......... 433/215 |
| 6,440,122 B1 | | 8/2002 | Shimoji |
| 7,184,150 B2 | * | 2/2007 | Quadling et al. ............. 356/602 |
| 7,202,490 B2 | | 4/2007 | Aguirre et al. |
| 7,940,260 B2 | * | 5/2011 | Kriveshko ..................... 345/419 |
| 2006/0269897 A1 | * | 11/2006 | Gill et al. ........................ 433/29 |
| 2007/0134615 A1 | * | 6/2007 | Lovely ............................ 433/29 |

(Continued)

OTHER PUBLICATIONS

European Patent Office, European Search Report issued in corresponding European Application No. 13180085.6, dated Nov. 27, 2013, 4 pp.

*Primary Examiner* — Ralph Lewis
(74) *Attorney, Agent, or Firm* — Wood, Herron & Evans, LLP (57) ABSTRACT

The method of curing a dental composite includes forming a composite filling in a cavity of a tooth surface by filling the cavity with an uncured composite and determining the geometry of the composite filling, including locations of interfaces between the composite filling and the tooth surface. The method further includes calculating a predetermined polymerization pattern for minimizing shrinkage stress at the interfaces, based on the geometry of the composite filling, and scanning a focused laser beam across the composite filling in accordance with the predetermined polymerization pattern to selectively and progressively cure the composite filling.

20 Claims, 7 Drawing Sheets

(56) References Cited

U.S. PATENT DOCUMENTS

2009/0323733 A1 12/2009 Charkas
2010/0216089 A1 8/2010 Cao
2014/0272775 A1* 9/2014 Monty ............................ 433/29

* cited by examiner

SCANNING POLYMERIZATION OF DENTAL MATERIAL

CROSS REFERENCE TO RELATED APPLICATION

Pursuant to 37 CFR §1.78(a)(4), this application claims the benefit of and priority to prior filed Provisional Application Ser. No. 61/683,556, filed Aug. 15, 2012, which is expressly incorporated herein by reference in its entirety.

FIELD OF THE INVENTION

This invention relates to a method and system for curing dental materials.

BACKGROUND OF THE INVENTION

Light curing restorations are commonly used in dental applications. As part of a typical dental procedure, a composite is dispensed in a tooth cavity, and the composite is hardened or cured with a dental curing light. In conventional systems, halogen or LED curing lamps are used to flood an entire tooth with light so as to cure an entire area of the composite simultaneously. Such flooding of light indiscriminately illuminates the tooth with unfocused light, which makes it challenging to control shrinkage behavior of the composite.

The curing light activates polymerization of the composite as a function of light intensity throughout the cavity. As the composite polymerizes, it naturally shrinks due to formation of covalent bonds and reduction in free volume. When the entire composite starts to polymerize at once, the composite material is trapped in an energetically less stable state in which it does not have enough time and mobility to relax. On the other hand, the composite is bonded or adhered to cavity walls in order to secure the restoration in place and seal a margin or interface. These two phenomena—i.e., total shrinkage of the composite and adhesion to the cavity walls—result in strain, which consequently induces stress on the cavity walls. Such stress concentration at the interfaces between the composite and the cavity walls, referred to as the margins, may result in immediate or delayed debonding, which may result in a number of clinical issues, such as secondary caries. In general, debonding may reduce lifetime and effectiveness of the restoration. Such stress at the interfaces may also lead to post-operative pain and/or sensitivity for the patient.

Current methods of dealing with the problem of uncontrolled stress on the cavity walls may include using a layer filling technique, applying liners in the cavity base, employing light soft-start illumination strategies (e.g., ramp cure), and/or using flowable or low shrinkage composites. Although composites with reduced shrinkage have been developed recently, overall shrinkage and the shrinkage stress for dental materials are still not ideal.

SUMMARY OF THE INVENTION

The present invention provides a method of curing a dental composite including forming a composite filling in a cavity of a tooth surface by filling the cavity with an uncured composite comprising a polymerization initiator and determining a geometry of the composite filling, including locations of interfaces between the composite filling and the tooth surface. The method further includes calculating a predetermined polymerization pattern for minimizing shrinkage stress at the interfaces, based on the geometry of the composite filling, and scanning a focused laser beam configured to activate the polymerization initiator across the composite filling in accordance with the predetermined polymerization pattern to selectively and progressively cure the composite filling.

BRIEF DESCRIPTION OF THE DRAWINGS

The accompanying drawings which are incorporated in and constitute a part of this specification, illustrate embodiments of the invention and, together with a general description of the invention given above, and the detailed description given below, serve to explain the invention.

DETAILED DESCRIPTION

With reference to the figures, apparatus and techniques used in scanning polymerization of a dental material or composite are shown. The term "composite," as used herein, is defined as a restorative material that is activated through absorption of light or heat and can include a dental bonding agent, a cement, or another material with similar properties, as known to one of ordinary skill. Use of the term "composite" should not be considered limiting, however, as the invention described herein applies broadly to dental materials.

Figure 1:
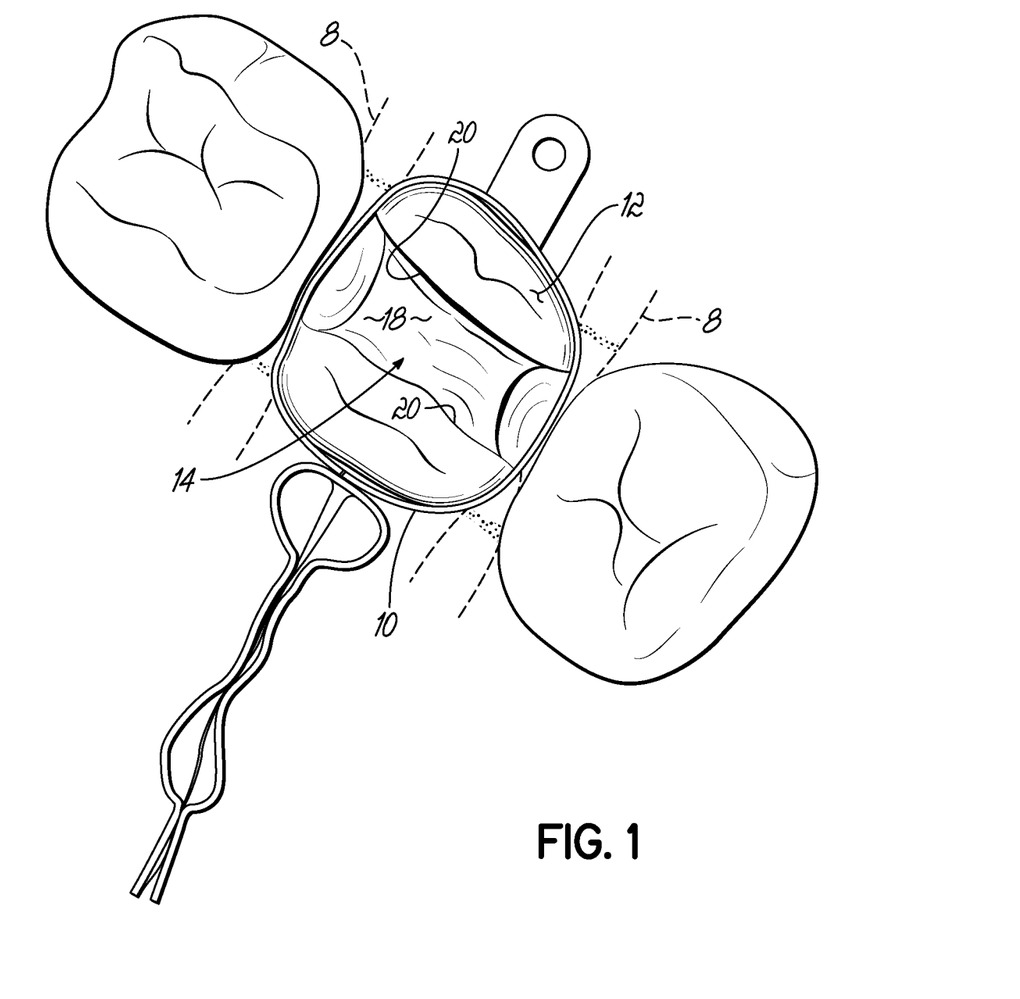
FIG. 1 is a top view of an unfilled cavity in a tooth.
Figure 2:
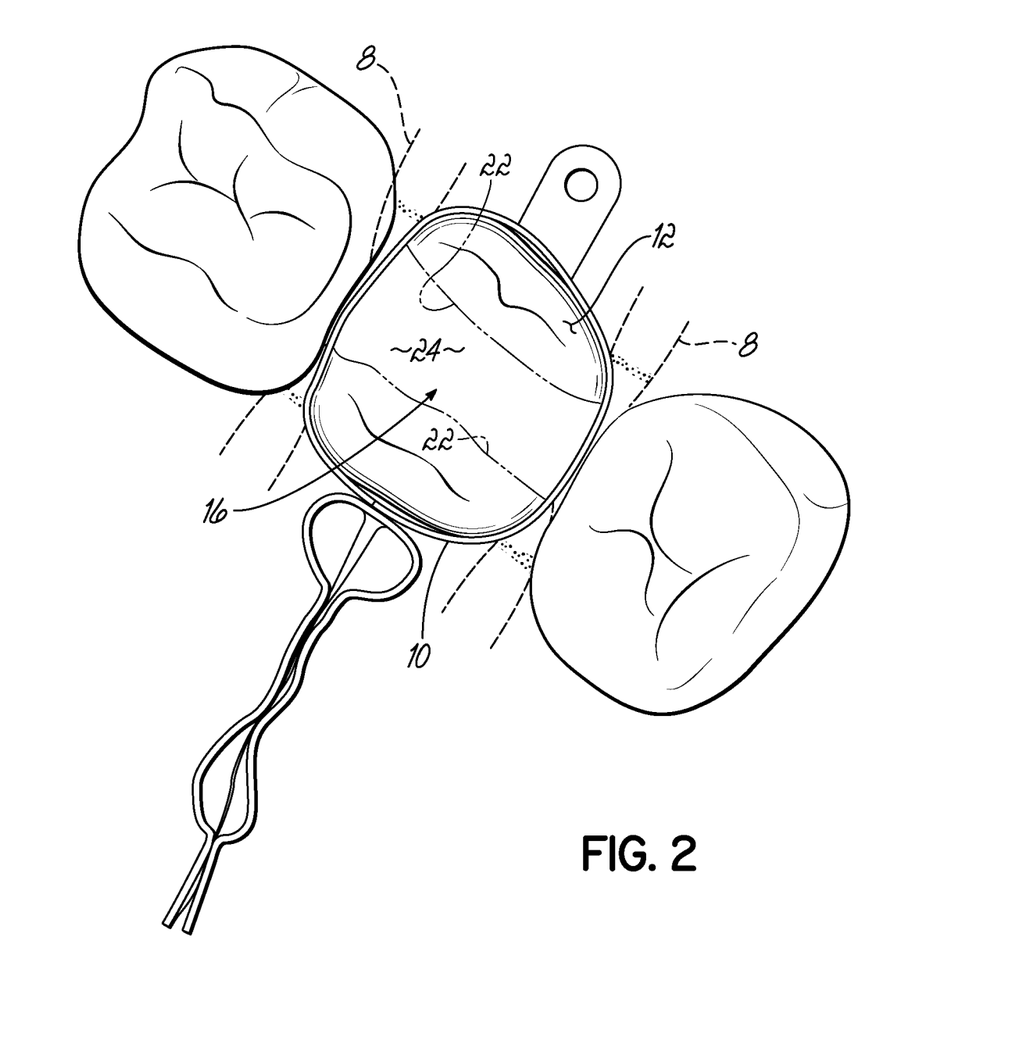
FIG. 2 is a top view of the cavity of FIG. 1 filled with uncured dental composite.

With reference to FIGS. 1 and 2, in an embodiment of the invention, conventional spacers 8 (shown in phantom) and a conventional matrix band 10 may be positioned around a tooth 12 having a cavity 14 that is to be filled with composite 16. The cavity 14 has a base 18 and side walls 20. Once the matrix band 10 is positioned on the tooth 12, the cavity 14 is filled with uncured composite 16 including one or more polymerization initiators, such as camphorquinone (CQ), and/or heat curable resins by methods known in the art. The composite 16 may be bulk fill, such as that used in the Kerr® SonicFill® system. It is not necessary for a layering technique to be employed. Interfaces 22 are created between the composite filling 16 and the tooth surface (i.e., the base 18 and side walls 20 of the cavity 14). In premolars, for example, a top surface 24 of the composite filling 16 may be generally planar with a top surface of the tooth 12.

With reference now to FIGS. 3-5B, a scanning head assembly (not shown) may be used to determine a size and a shape of the composite filling 16. In particular, locations of the interfaces 22 are determined. The scanning head assembly may be mounted on the matrix band 10, on a bite attachment (not shown), or on an adjustable fixture (not shown) attached to one or more neighboring teeth so as to be secured or held in place within the oral cavity. In an embodiment, the scanning head assembly may include an image capturing device, such as a micro-camera, that obtains digital imaging data of the composite filling 16 and/or the cavity base 18 and walls 20. The camera may be equipped with a wide lens. In another embodiment, an intraoral scanner, such as an occlusal composite shape scanner, may prepare a digital scan that shows three-dimensional contouring of the composite filling 16. In yet another embodiment, a non-polymerizing laser scanning source, such as a red laser beam, may scan the composite filling 16. A response of the non-polymerizing laser beam may be captured by the micro-camera. The imaging or scanning of the composite filling may be referred to as a "pre-scan."

Figure 3:
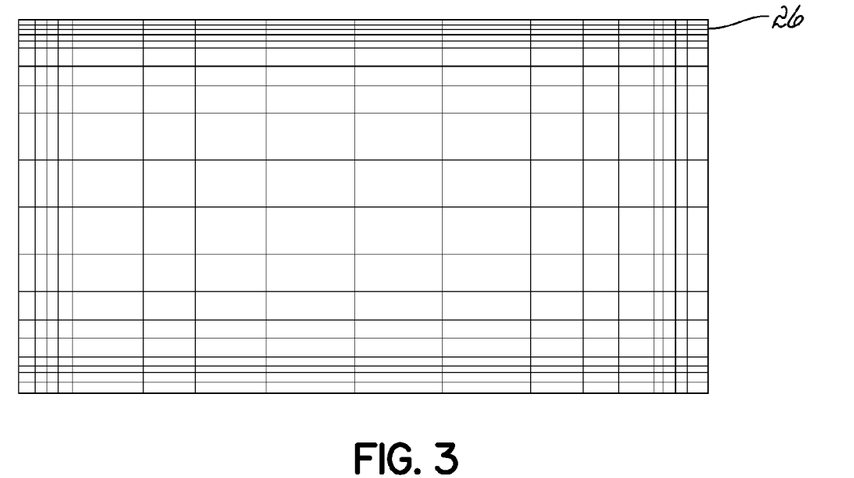
FIG. 3 is a schematic diagram of a mesh generated from a scan of a cavity filled with a dental composite.

After the pre-scan captures an image or scan of the composite filling 16, digital data from the image or scan may be inputted into a data processor, such as a central processing unit (CPU) (not shown) or a microprocessor (not shown), as x, y, and z coordinates. The data processor evaluates the digital data in order to generate the geometry of the composite filling 16. With reference to FIG. 3, in an embodiment, the generated image or scan of the cavity 14 may be processed into mesh vertices 26. The horizontal and/or vertical gridlines of the mesh 26 may be more densely drawn near the interfaces 22 between the composite filling 16 and the cavity walls 20, i.e., at the margins, than in an interior of the composite filling 16. In this way, the mesh vertices 26 may be utilized to optimize a laser polymerization pattern strategy for imposing minimal stress on the cavity walls 20. An optimal polymerization pattern may be calculated as a function of one or more predefined algorithms.

Based on input from the data processor, a laser scanning assembly, such as Lemoptix's MVIEW® Microprojector, for example, may be used to selectively scan a laser beam 30 across the composite filling 16 according to the predetermined polymerization pattern. The laser scanning assembly includes hardware and firmware. The laser scanning assembly is small enough to fit within the oral cavity for positioning over a particular tooth 12. For example, the laser scanning assembly may have an optical engine volume of approximately 1.5 cm$^3$ with dimensions of 5×12×25 mm.

The laser scanning assembly includes a laser source 32 and a minor assembly 34, as shown in FIGS. 6A and 6B. The laser source 32 may be positioned at a proximal end of a device 40 that houses the assembly, or, alternatively, the laser beam 30 may be transferred from outside the mouth to the oral cavity via optical fibers (not shown), for example. The mirror assembly 34 is positioned at a proximal end of the device 40. The minor assembly 34 may comprise two-dimensional, magnetically-driven micro-minors. The laser scanning assembly may contain a chip with an application-specific integrated circuit (ASIC) and/or a field programmable gate array (FPGA). Therefore, the chip may be freely programmed according to specific application requests for the laser beam 30 polymerization pattern.

Figure 4A:
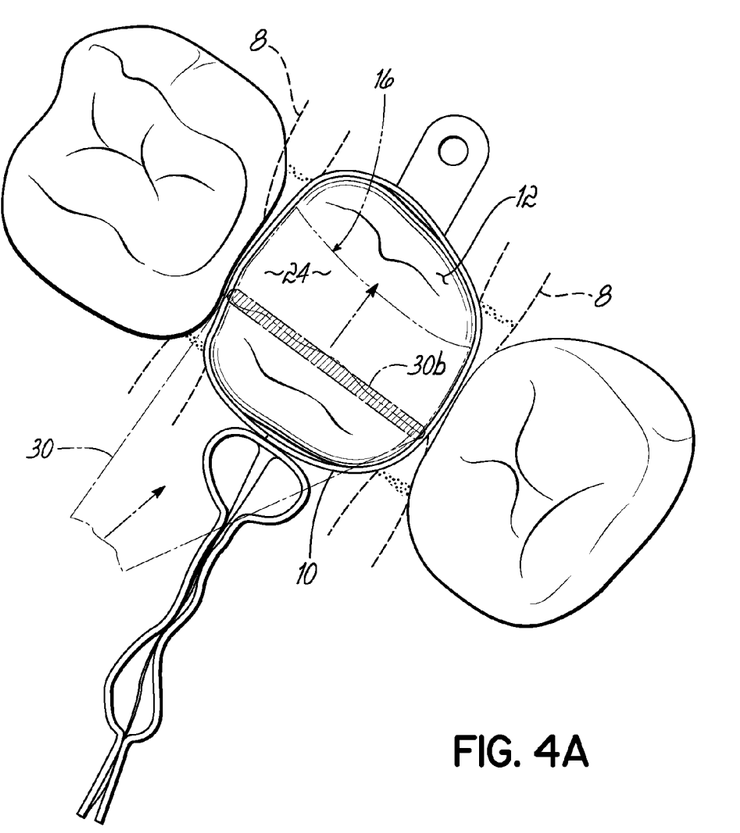
FIG. 4A is a top view of a laser beam scanning the cavity of FIG. 2 according to an embodiment.
Figure 4B:
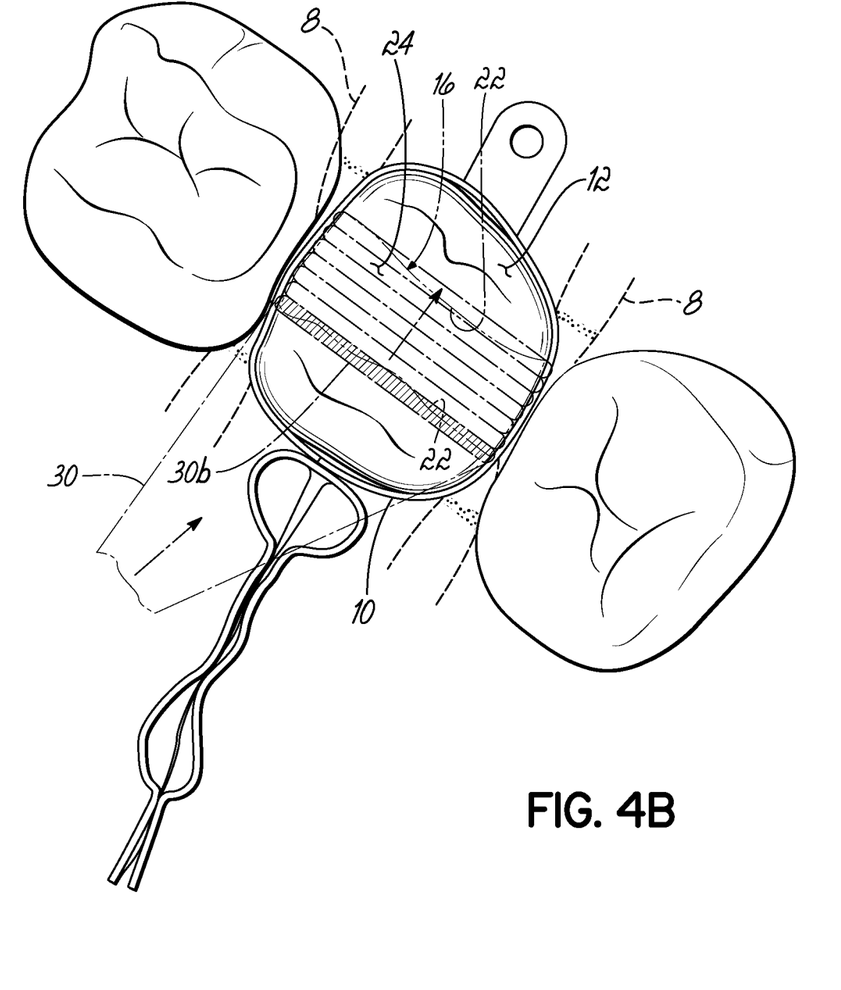
FIG. 4B is a top view of a laser beam scanning the cavity of FIG. 2 according to another embodiment.
Figure 4C:
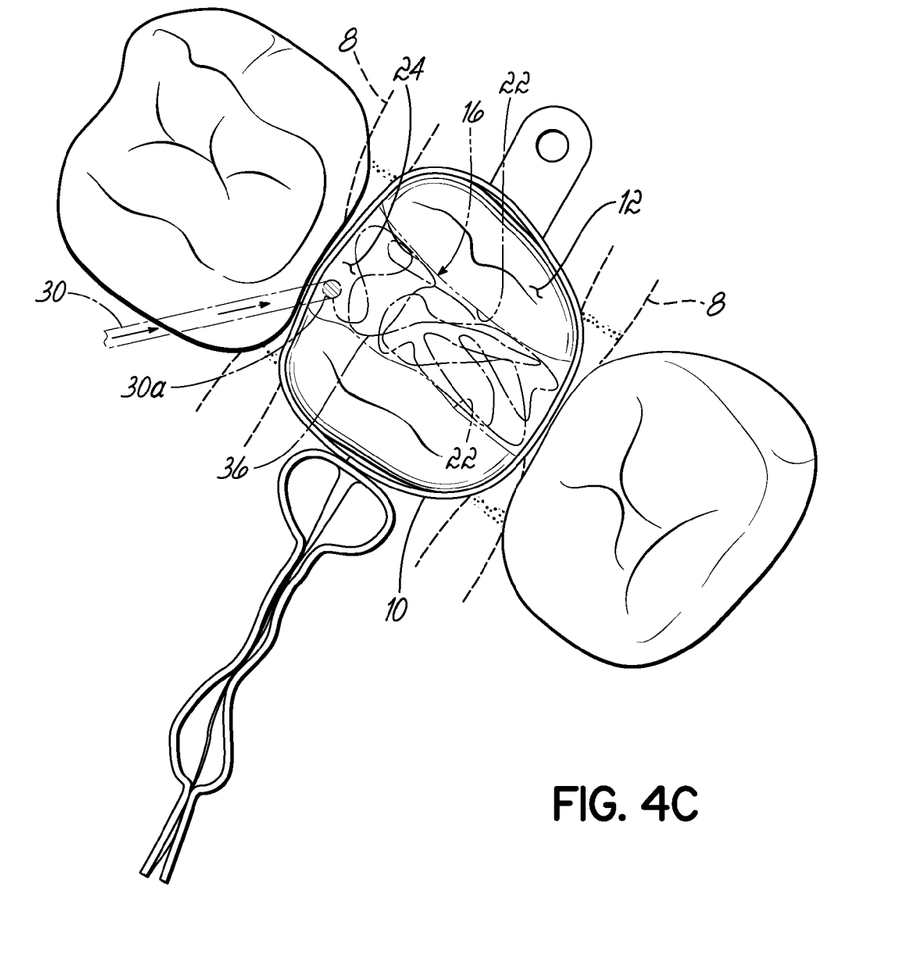
FIG. 4C is a top view of a laser beam scanning the cavity of FIG. 2 according to yet another embodiment.
Figure 4D:
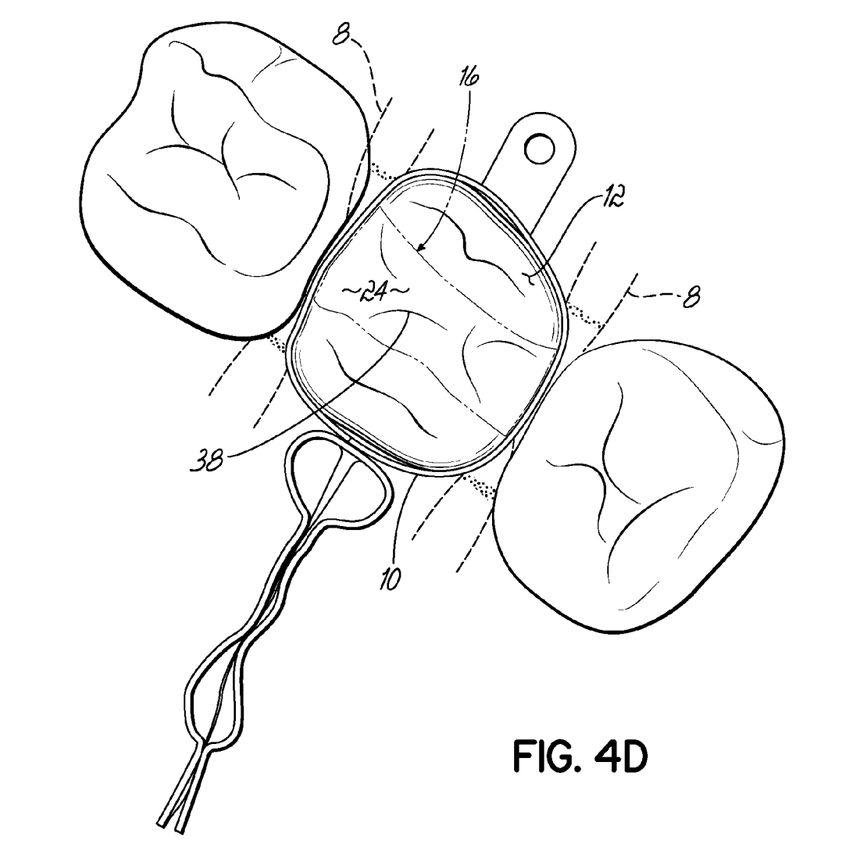
FIG. 4D is a top view of the cavity of FIG. 2 filled with a cured dental composite.

With reference now to FIGS. 4A-4C, a variety of types of lasers may be used in the laser scanning assembly (described in further detail below). For example, the scanning assembly may include an integrated semiconductor laser (e.g., a laser diode). Alternatively, a conventional light source may be used with the laser scanning assembly. One of ordinary skill will recognize that the output power of the laser source 32 may vary depending on the specific application, including a formulation of the composite 16. The laser source 32 may operate in a wide range—for example, less than 5 mW to greater than 1000 mW (i.e., 1 W). However, the laser source 32 may be operated to have a maximum output power of approximately 200 mW or higher. In one embodiment, the laser source 32 may be operated to have an output power in the range of 50-150 mW. The output power should be selected to avoid any undesired thermal influence on the composite filling 16. One of ordinary skill will recognize that an effective power output may be lower than the output power. For example, if the output power is 100 mW, after reflection on the mirror assembly 34, the effective power may be 85 mW. The power consumption of a 80 mW laser source 32 may be approximately 800 mW, and the power consumption of the minor assembly 34 may be approximately 80 mW. Moreover, there may be internal power losses due to scattering, absorption, etc. in the composite filling 16. For example, the light reflection may be at least 85%, and thus a power loss of the laser beam 30 may be approximately 15%.

One of ordinary skill will also recognize that a wavelength of the scanning laser beam 30 may vary depending, for example, on the formulation of the composite filling 16. For example, a blue curing light having a wavelength in the range of 400-500 nm may be used depending on the type of polymerization initiator in the composite 16. For example, in an embodiment in which the composite 16 formulation includes CQ as the photoinitiator, a wavelength of approximately 465 nm may be used. In another embodiment, wavelengths in a range between ultraviolet (UV) to near infrared may be used. Alternatively, in another embodiment, the laser beam 30 may be used as a source of heat for a composite including a heat curable resin, rather than a photoinitiator.

In an embodiment, a microelectromechanical system (MEMS) tunable laser may be used as laser source 32 to enable laser assembly operation with a variety of colors of lasers or over a wide range of wavelengths. The MEMS tunable laser may be used to generate both a non-polymerizing laser beam for the pre-scan and a polymerizing laser beam 30 for curing the composite filling 16. In another embodiment, the MEMS tunable laser may be used to activate a plurality of different polymerization initiators in a composite filling 16. For example, in a composite filling 16 having two polymerization initiators, the MEMS tunable laser may scan a laser beam 30 having a first wavelength sufficient to activate a first polymerization initiator in the composite, then the MEMS tunable laser 32 may adjust the wavelength and perform a second scan that is sufficient to activate a different polymerization initiator in the composite filling 16.

In an embodiment, the laser scanning assembly generates a focused or collimated laser beam 30 as a point beam 30a or beam line 30b, for example. The point beam 30a may have a diameter of approximately 0.5 mm. A laser beam line 30b may also be generated from a line scan of the focused point beam 30a. The laser beam line 30b illuminates the cavity 14 longitudinally. The beam line 30b may be approximately 5-6 mm long, for example. However, the laser beam line 30b length may be adjusted with a trimmer (not shown) or through other means. Scanning the focused laser beam 30 activates the polymerization initiator in the composite filling 16 to induce curing. By using a focused laser beam 30, the power and light are confined to a small region and focal point, which provides increased control over the curing location.

The programmed laser scanning assembly may control the scanning of the laser beam 30 in a predetermined polymerization pattern across the composite filling 16. With reference now to FIGS. 4A-4C, multiple polymerization patterns are possible. For example, as shown in FIG. 4A, the laser beam line 30b may be scanned as a continuous progression across the composite filling 16. In another embodiment, as shown in FIG. 4B, the laser beam line 30b may be scanned in a step-by-step fashion across the composite filling 16. With either of the continuous or step-by-step progression embodiments, the mesh vertices 26 described above may be utilized to employ a scanning pattern that cures parallel to the interfaces 22. In another embodiment, as shown in FIG. 4C, the laser point beam 30a may be moved according to a predetermined path 36 within the bounds of the composite filling 16. One of ordinary skill will recognize a variety of other scanning patterns that may be used. The scanning patterns permit a progressive curing of the composite, with selective curing in the localized area of the laser beam 30 occurring as the laser beam 30 is progressively scanned. Thus, the invention enables a highly controlled selective and progressive cure of the composite filling 16.

Although a total scanning time for the composite filling 16 will vary depending on the laser output power, 20 seconds may be a sufficient time to progressively cure the composite filling 16. In one embodiment, scanning occurs for 10-40 seconds. In another embodiment, scanning occurs for 15-30 seconds. In an embodiment, the laser beam 30 may scan over certain areas of the composite filling 16 longer than others or may scan over certain areas more than once. For example, the laser beam may spend additional scanning time proximate the interfaces 22 or in areas of the filling having a greater depth of composite 16.

By using a progressive polymerization pattern, one may significantly reduce shrinkage stress of the composite filling 16. Because the use of a scanning pattern for curing selectively polymerizes only a portion of the composite filling 16 at a time, only that portion of the composite 16 experiences shrinking at a given time, while a remainder of the composite 16 that is uncured has time to adapt and significantly reduce overall stress on the cavity 14. Although a total amount of stress may be equal to that experienced with flooding polymerization by an LED lamp, the distribution of the shrinkage is improved by not polymerizing the entire composite 16 at once. Test results have demonstrated an approximately 50% reduction in shrinkage stress compared to conventional polymerization.

The stress distribution may also be improved by curing the interfaces 22 first, for a greater duration of time, and/or with a denser polymerization pattern than in the interior of the composite filling 16. For example, by curing the interfaces 22 of the composite filling 16 first, non-cured composite 16 may flow to or back fill the polymerized interfaces 22 to help compensate for shrinkage in those areas. In this way, the shrinkage may be at least partially transferred from the interfaces 22 to the interior of the composite filling 16. Shrinkage at the interior of the composite filling 16 may result in "crater-like" features 38 (FIG. 4D) on the surface 24 thereof, but shrinkage at the interior of the composite filling 16 may not result in a considerable amount of residual stress or is otherwise less detrimental than shrinkage at the interfaces 22.

The selective and controlled polymerization shrinkage behavior that results from this method of scanning a focused laser beam 30 may provide several advantages. For example, a decrease in lateral shrinkage stress may reduce post operative pain and/or sensitivity, occurrence of open margins, and/or occurrence of secondary caries.

Figure 5A:
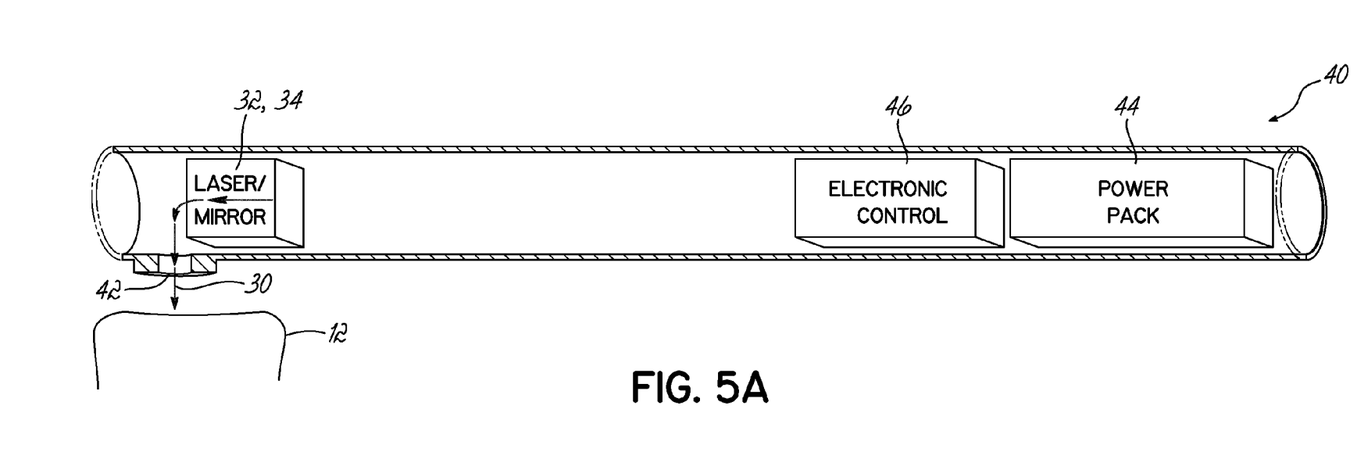
FIG. 5A is a schematic diagram of an embodiment of a laser scanning device.
Figure 5B:
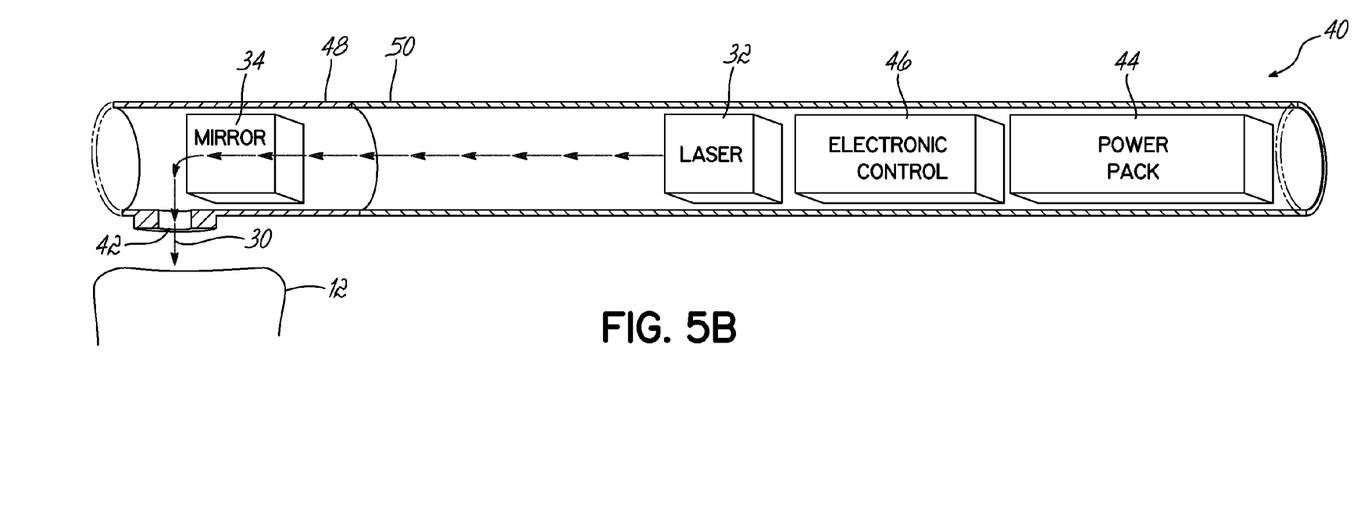
FIG. 5B is a schematic diagram of another embodiment of a laser scanning device.

As shown in FIGS. 5A and 5B, the laser scanning assembly described above may be integrated into a handheld device 40 that may be partially or completely secured in the oral cavity. As an example of relative size, the handheld device 40 may have a length of approximately 180 mm and a diameter of approximately 15 mm. With reference to FIG. 5A, a one-piece handheld device 40 may include the laser scanning assembly, including the laser source 32 and the mirror assembly 34, positioned proximal the tooth 12. At the proximal end of the device 40 is an aperture 42 through which the laser beam 30 is emitted. A power pack 44 may be positioned at the distal end of the device 40, and an electronic control 46 may be positioned intermediate the power pack 44 and the laser scanning assembly. In this embodiment, the laser scanning assembly is situated inside the oral cavity, and the power pack 44 and the electronic control 46 are situated outside the oral cavity when the device 40 is in use. An exterior of the device 40 may be at least partially covered by a protective sleeve (not shown).

In an alternative embodiment of the handheld device 40 shown in FIG. 5B, the device 40 may comprise two separable pieces 48, 50. The mirror assembly 34 of the laser scanning assembly may be included in the piece 48 comprising the proximal portion of the device 40, which may be separated from the other piece 50 comprising the distal portion of the device 40. The laser source 32 may be spaced from the mirror assembly 34 in the other piece 50 of the device 40. The power pack 44 may be positioned at the distal end of the piece 50, the laser source 32 may be positioned nearer the proximal end of the piece 50, and an electronic control 46 may be positioned intermediate the power pack 44 and the laser source 32. In this embodiment, the mirror assembly 34 is situated inside the oral cavity, but the power pack 44, electronic control 46, and the laser source 32 are situated outside the oral cavity when the device 40 is in use. Because the piece 48 including the minor assembly 34 is separable from the remaining components of the handheld device 40, the mirror assembly 34 is capable of being autoclaved for sterilization.

Figure 6:
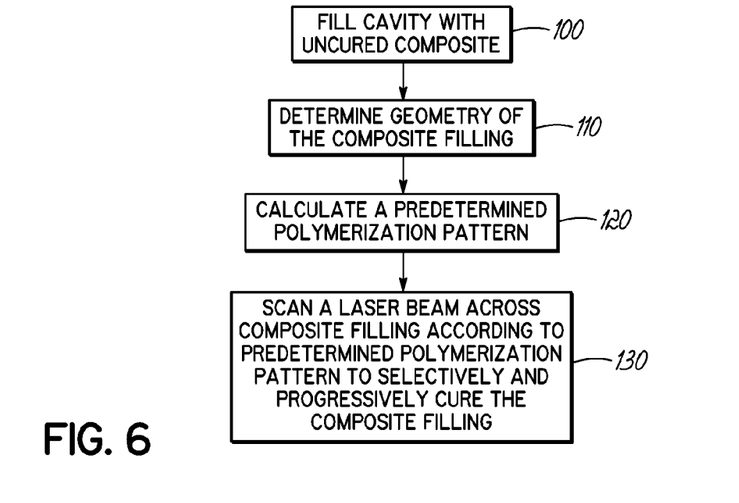
FIG. 6 is a flow chart of a method of the invention.

In an embodiment of the invention, a method is provided for curing a dental composite, which method is illustrated in the flowchart of FIG. 6. In 100, the cavity in a tooth surface is filled with an uncured composite that comprises a polymerization initiator to form a composite filling. In 110, the method includes determining the geometry of the composite filling, including the locations of interfaces between the composite filling and the tooth surface. In 120, based on the determined geometry, a predetermined polymerization pattern is calculated for minimizing shrinkage stress at those interfaces. In 130, the method includes scanning a laser beam across the composite filling according to the predetermined polymerization pattern to both selectively and progressively cure the composite filling. As discussed above, the laser beam may be a point beam or a beam line to selectively cure the composite filling in the localized area of the point beam or beam line as the laser beam is progressively scanned across the composite filling.

In one embodiment, the laser beam is scanned parallel to and at the interfaces first and then progressively away from the interfaces toward the interior of the geometry. In one embodiment, the progression is step-by-step, and in another embodiment, the progression is continuous.

In one embodiment, the scanning in 130 is repeated at one or more additional wavelengths configured to activate additional polymerization initiators contained in the composite filling. Thus, a first scan of the laser beam may activate a first polymerization initiator at a first wavelength, while a second scan of the laser beam may activate a second polymerization initiator at a second wavelength different from the first wavelength. Any number of polymerization initiators may be used having different activation wavelengths. In addition, the multiple polymerization initiators may be photoinitiators or heat curable resins, such that each scan of the laser beam may be configured to activate one of the polymerization initiators by either light or heat.

In one embodiment, in 110, the geometry of the composite filling is determined by scanning the composite filling with a scanning assembly configured to obtain digital imaging data. The data is inputted to a data processor for evaluation to generate the geometry. In one embodiment, the scanning assembly includes an image capturing device, such as a micro-camera. The scanning assembly may include a non-polymerizing laser source, with the micro-camera capturing the response of the laser source. In one embodiment, the data processor calculates the predetermined polymerization pattern as a function of pre-defined algorithms. In one embodiment, the data processor may generate the geometry into mesh vertices having more dense patterns near the interfaces and less dense patterns away from the interfaces.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. A method of curing a dental composite, comprising:
    forming a composite filling in a cavity of a tooth surface by filling the cavity with an uncured composite comprising a polymerization initiator;
    pre-scanning the composite filling with a scanning assembly to obtain imaging data;
    inputting the imaging data into a data processor, which evaluates the imaging data to generate a geometry of the composite filling, including locations of interfaces between the composite filling and the tooth surface, and based on the geometry, calculates a predetermined polymerization pattern for minimizing shrinkage stress at the interfaces; and
    scanning a focused laser beam configured to activate the polymerization initiator across the composite filling in accordance with the predetermined polymerization pattern to selectively and progressively cure the composite filling.

2. The method of claim 1, wherein the scanning assembly includes an image capturing device.

3. The method of claim 2, wherein the scanning assembly includes a non-polymerizing laser source that pre-scans the composite filling, and the image capturing device captures the response of the non-polymerizing laser source.

4. The method of claim 1, wherein a microelectromechanical system tunable laser is used for at least one of the pre-scanning and scanning steps.

5. The method of claim 1, wherein the data processor calculates the predetermined polymerization pattern as a function of pre-defined algorithms.

6. The method of claim 1, wherein the data processor processes the generated geometry into mesh vertices having a dense pattern near the interfaces and a less dense pattern in an interior of the geometry, and the mesh vertices are utilized in calculating the predetermined polymerization pattern.

7. The method of claim 6, wherein the laser beam is focused as a beam line, and the scanning is performed with the beam line initially parallel to and at the interfaces and proceeds progressively away from the interfaces toward the interior of the geometry.

8. The method of claim 7, wherein the scanning is performed as a step-by-step progression.

9. The method of claim 7, wherein the scanning is performed as a continuous progression.

10. The method of claim 7, wherein a duration of the scanning is longer proximate the interfaces than in the interior of the geometry.

11. The method of claim 1, wherein the laser beam is focused as a point beam, and the scanning is performed as a continuous progression.

12. The method of claim 1, wherein an output power of the laser beam is less than or equal to 200 mW.

13. The method of claim 12, wherein the output power of the laser beam is in the range of 50-150 mW.

14. The method of claim 1, wherein a total duration of the scanning is approximately 15-30 seconds.

15. The method of claim 1, wherein a duration of the scanning is longer for areas of the composite filling having a greater depth of the uncured composite.

16. The method of claim 1, wherein the scanning is at a first wavelength sufficient to activate the polymerization initiator, and further comprising:
    scanning the focused laser beam at a second wavelength sufficient to activate a second polymerization initiator subsequent to scanning the focused laser beam at the first wavelength, wherein the second wavelength is different from the first wavelength.

17. The method of claim 16, wherein a microelectromechanical system tunable laser is used for scanning the focused laser beam at the first and second wavelengths.

18. A method of curing a dental composite, comprising:
    forming a composite filling in a cavity of a tooth surface by filling the cavity with an uncured composite comprising a polymerization initiator;
    pre-scanning the composite filling with a non-polymerizing laser source and capturing a response of the non-polymerizing laser source with an image capturing device to obtain digital imaging data;
    inputting the digital imaging data into a data processor, which evaluates the digital imaging data to generate a geometry of the composite filling, including locations of interfaces between the composite filling and the tooth surface, and calculates from that geometry a predetermined polymerization pattern for minimizing shrinkage stress at the interfaces; and
    progressively scanning a laser beam focused in a beam line across the composite filling parallel to the interfaces and in accordance with the predetermined polymerization pattern, the laser beam having a wavelength configured to active the polymerization initiator.

19. The method of claim 18, wherein the progressive scanning begins proximate the interfaces and continues toward an interior of the geometry, with the scanning having a longer duration at the interfaces than in the interior.

20. A method of curing a dental composite, comprising:
    forming a composite filling in a cavity of a tooth surface by filling the cavity with an uncured composite comprising a polymerization initiator;
    pre-scanning the composite filling with a scanning assembly to obtain imaging data;
    inputting the imaging data into a data processor, which evaluates the imaging data to generate a geometry of the composite filling, including locations of interfaces between the composite filling and the tooth surface, and based on the geometry, calculates an optimal polymerization pattern specifically for the composite filling so as to minimize shrinkage stress at the interfaces; and
    scanning a focused laser beam configured to activate the polymerization initiator across the composite filling in accordance with the optimal polymerization pattern to selectively and progressively cure the composite filling.

* * * * *

UNITED STATES PATENT AND TRADEMARK OFFICE
CERTIFICATE OF CORRECTION

PATENT NO. : 8,992,224 B2
APPLICATION NO. : 13/839995
DATED : March 31, 2015
INVENTOR(S) : Beat Kilcher et al.

Page 1 of 1

It is certified that error appears in the above-identified patent and that said Letters Patent is hereby corrected as shown below:

In the Specification:

In Col. 3, line 47, "minor assembly 34" should read --mirror assembly 34--.

In Col. 3, line 48, "micro-minors." should read --micro-mirrors.--.

In Col. 4, line 9, "minor assembly 34" should read --mirror assembly 34--.

In Col. 6, line 25, "minor assembly 34" should read --mirror assembly 34--.

In the Claims:

In Col. 8, line 43, Claim 18, "to active" should read --to activate--.

Signed and Sealed this
Fourteenth Day of July, 2015

Michelle K. Lee
*Director of the United States Patent and Trademark Office*